US00PP10786P

United States Patent [19]

Osiecki

[11] Patent Number: Plant 10,786

[45] Date of Patent: Feb. 9, 1999

[54] SPATHIPHYLLUM PLANT 'S2'

[75] Inventor: Marian W. Osiecki, Marianna, Fla.

[73] Assignee: Oglesby Plants International, Inc., Altha, Fla.

[21] Appl. No.: 858,489

[22] Filed: May 19, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,677 10/1996 Osiecki ..... Plt./88.1
P.P. 9,901 5/1997 Osiecki ..... Plt./88.1
P.P. 10,008 8/1997 Osiecki ..... Plt./88.1
P.P. 10,013 11/1997 Osiecki ..... Plt./88.1

*Primary Examiner*—Howard J. Locker
*Assistant Examiner*—Kent L. Bell
*Attorney, Agent, or Firm*—Rothwell, Figg, Ernst & Kurz

[57] ABSTRACT

A new and distinct cultivar of Spathiphyllum is provided. The plant is medium to large size, relatively open; suitable for production in a 15–25 cm pot from a single tissue culture produced microcutting; grows vigorously; branches early; naturally flowers early, abundantly and year-round producing superior quality inflorescences from the onset of flowering. Spathes are large and held on very thick, strong peduncles.

2 Drawing Sheets

SUMMARY OF THE INVENTION

This invention relates to a new and distinct Spathiphyllum cultivar characterized by the following combination of repeatedly observed traits:

1. Medium to large size,
2. relatively open and upright growth habit,
3. vigorous growth,
4. early branching,
5. early, abundant and year-round natural flowering,
6. inflorescence of a superior quality from the onset of flowering,
7. thick, strong peduncles,
8. large spathes retaining upright position past maturity;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plant Laboratories, Inc. near Altha, Fla. The female parent was a selected clone of Spathiphyllum 'Linda' (unpatented) and the male parent was a selected clone of Spathiphyllum 'Petite' (unpatented). The cross was made in 1991. The plant was selected in 1992 and has been asexually reproduced by tissue culture in the vicinity of Altha, Fla. since 1993 with the characteristics stated, found to be maintained through successive generations. The plant is a sibling of Spathiphyllum 'S16', which is described in co-pending U.S. Plant patent application Ser. No. 08/859,466.

This new cultivar has been identified as Spathiphyllum 'S2'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S2' was approximately 17.5 months from planting a single tissue culture produced microcutting and was grown in a 20 cm pot.

In the photographs:

DETAILED DESCRIPTION OF THE NEW CULTIVAR

Figure 1:
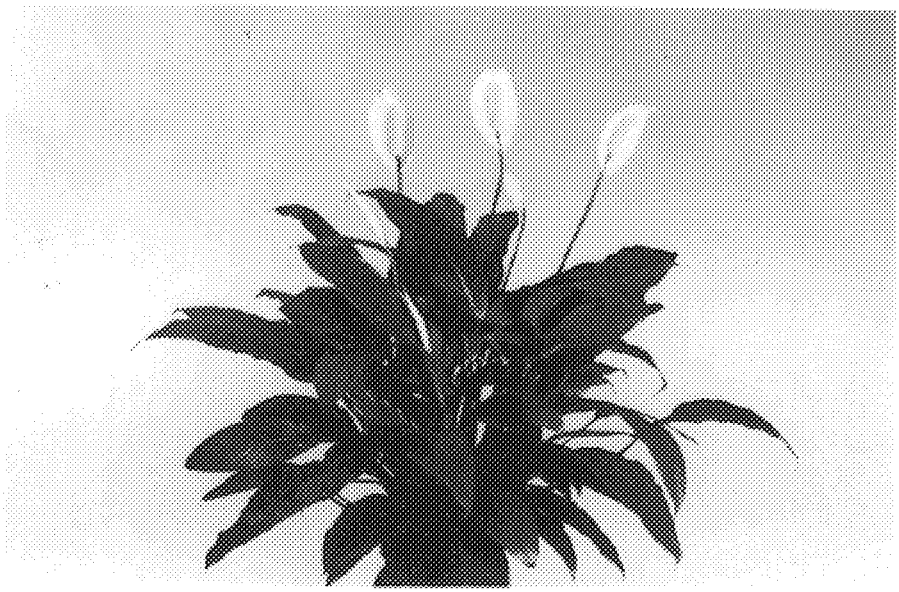
FIG. 1 depicts the whole plant.
Figure 2:
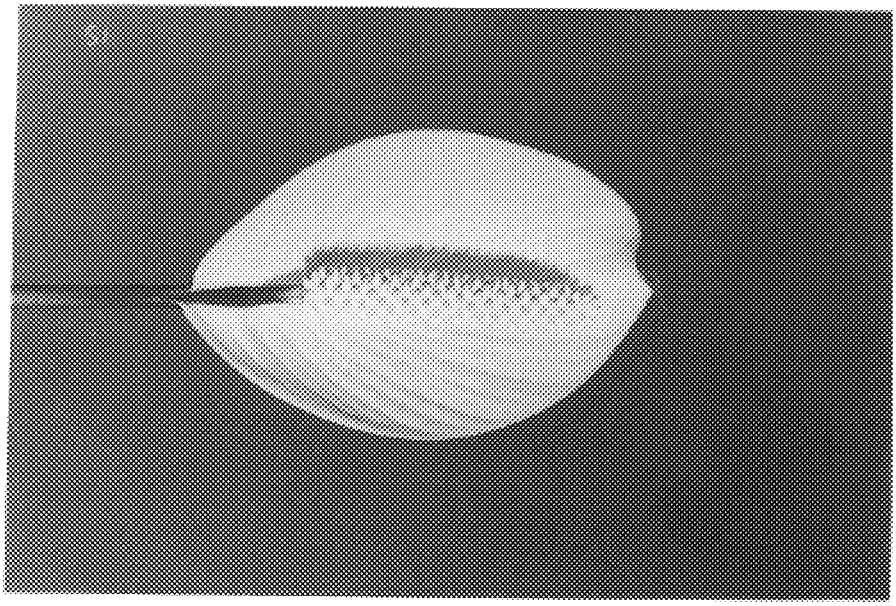
FIG. 2 illustrates the mature inflorescence.
Figure 3:
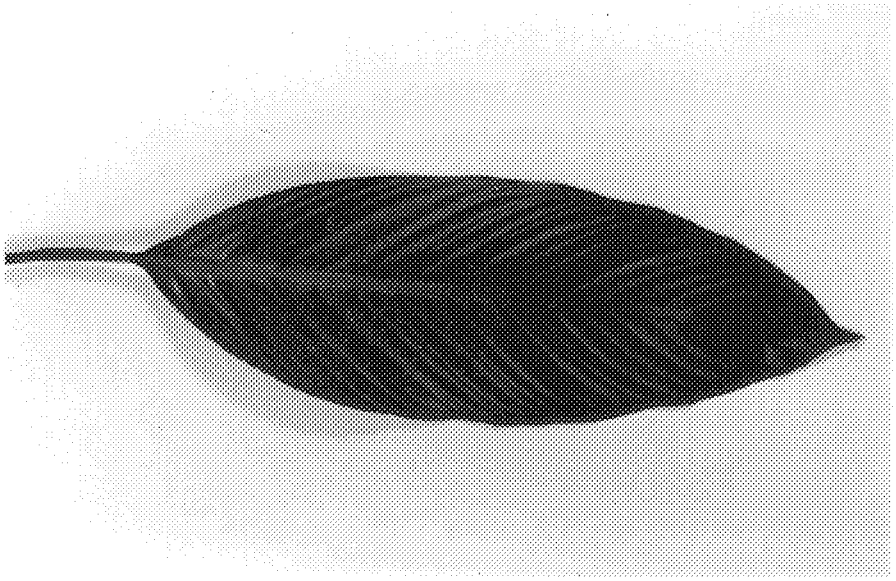
FIG. 3 illustrates the top of a mature leaf.
Figure 4:
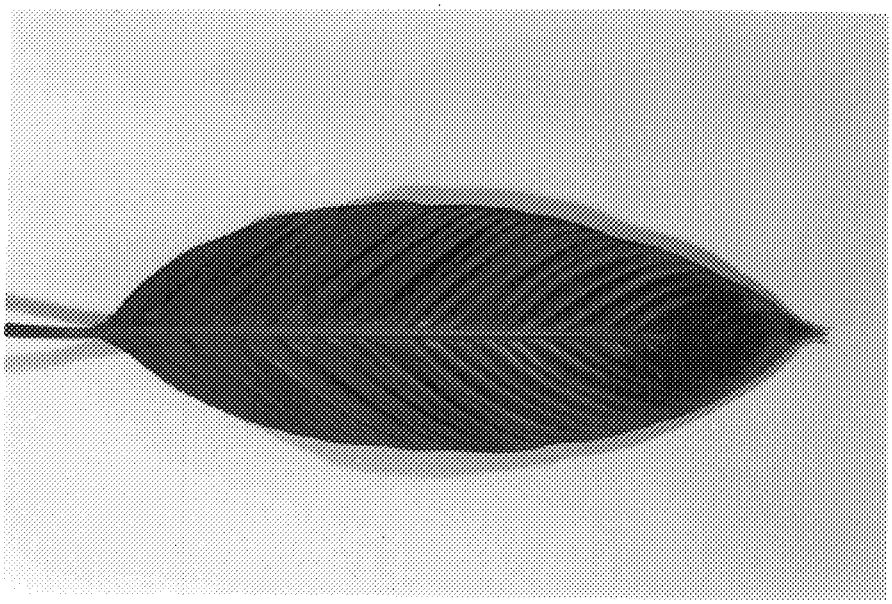
FIG. 4 illustrates the bottom of a mature leaf.

The following observations and measurements describe plants grown near Altha, Fla. under greenhouse conditions. These observations and measurements were recorded in February 1995 from mature plants (about 16 months from planting tissue culture produced microcuttings) grown in 20 cm pots. Fully developed organs were used for measurements. Color values were determined on Feb. 7, 1995 under natural, indirect light of approximately 350–430 foot-candles. Color references are made to The R.H.S. Colour Chart, except where general color terms of ordinary significance are used. 'S2' has not been observed under all possible environmental conditions. The phenotype may vary with variations in environment and horticultural practices, such as temperature, light intensity, day length, fertilization, propagation method, etc., without any change in genotype.

Botanical classification: Spathiphyllum hybrid cultivar 'S2'

Parentage:

*Female parent.*—Selected clone of Spathiphyllum 'Linda'.

*Male parent.*—Selected clone of Spathiphyllum 'Petite'.

Propagation: Plant tissue culture.

Plant descriptions:

*Growth habit.*—Medium to large size, relatively open and upright growth habit.

*Height.*—Foliage 42–53 cm; with spathes 69–79 cm.

*Diameter.*—76–91 cm.

Petiole:

Leaf supporting inflorescence.—24.0–37.0 cm long, 4.2–4.9 mm in diameter immediately below geniculum. Geniculum 3.0–4.0 cm long, 4.9–6.1 mm in diameter at the base.

*Leaf penultimate to leaf supporting inflorescence.*—21.2–31.0 cm long, 3.6–5.2 mm in diameter immediately below geniculum. Geniculum 3.3–4.7 cm long, 4.2–6.1 mm in diameter at the base.

Leaf blade:

*Shape.*—Elliptic, width divided slightly unequally by midrib; tip—acuminate, usually pointing downwards; base-cuneate, narrowly decurrent on petiole. Margin entire, slightly wavy.

*Size.*—Leaf supporting inflorescence: 26.2–31.5 cm long by 9.1–11.7 cm wide; length to width ratio 2.5–3.3:1.

Leaf penultimate to leaf supporting infloresence: 21.0–32.5 cm long by 8.1–11.0 cm wide; length to width ratio 2.5–3.0:1. Leaves produced at plant maturity are wider in proportion to their length than those produced at earlier stages.

*Texture.*—Smooth, glossy; young leaves highly polished.

*Veins.*—Well defined and sunken in the adaxial leaf surface.

*Color.*—Mature leaf: Adaxial: a little darker than 147 A (yellow-green). Abaxial: between 147 A and 147 B. Youngest unrolled leaf: Adaxial: between 137 A (green), 146 A (yellow -green) and 147A. Abaxial: 147B.

INFLORESCENCE:

*Arrangement.—Spathes carried on thick, strong peduncles. Spathe length to spadix length ratio* 1.6–2.1:1.

Peduncle:

*Size.*—46.5–65.5 cm long, 4.8–6.1 mm in diameter immediately below spathe. Stipe 3–9 mm long, 3.8–4.7 mm in diameter. Peduncle thins by less than 0.7 mm approximately 5.0–6.4 cm below spathe. Thinning zone is not conspicuous but often associated with slight bending of peduncle.

*Color.*—Front: 137 C (green) immediately below spathe. Back: A mixture of 137C (green), 147B and 146B (both yellow-green) near spathe; sometimes white color of spathe extends onto peduncle near juncture with stipe.

Spathe:

*Shape.*—Cupped, elliptic; tip-acuminate, twisted; base-cuneate to almost obtuse, variably asymmetric.

*Size.*—10.7–15.5 cm long, 6.5–7.8 cm wide and 1.9–2.4 cm deep; length to width ratio 1.6–2.0:1.

*Texture.*—Smooth, slightly glossy.

*Color.*—155D (white) with green coloration very limited on the front and more abundant on the back side. Back: Green midrib zone with poorly defined borders is approximately 4–6 mm wide at the juncture with the stipe, tapers to less than 1 mm about spathe mid-length and distally becomes a very fine line. The proximal part resembles 146 B-C, 147 B (both yellow-green), 137 C (green) with some 144 A (yellow-green) at the edges. 144 A dominates in the fine line of the distal half. Tip resembles 144 A and 146 B-C. Front: A green line approximately 0.2 mm wide is present in the distal portion of the spathe. In the tip some lateral veins and areas between them are also green. Spathe remains white for up to 5 weeks following bud appearance above foliage and then gradually changes to a green color.

Spadix:

*Size.*—5.7–7.8 cm long; 1.3–1.6 cm in diameter.

*Flower density.*—Approximately 4–6 flowers per linear 2-cm in mid-portion of spadix.

*Color.*—Determined by pistils' color. Varies between 158 C-D (yellow-white) and 159 C-D (orange-white).

Botanial Flower: *Size and shape.*—Perianth only slightly visible between thick pistils. Pistil elliptic with acute tip; approximately 5–5.5 mm long and 3–3.5 mm in diamater; protrudes approximately 2–3 mm beyond perianth; stigmas relatively large. Stamen approximately 2 mm long and 1–1.5 mm wide, with reduced filament. Stamens firmly pressed against the pistil and not visible above perianth until pollen release, at which time anthers protrude beyound perianth.

*Color.*—Perianth, pistil and stamen all yellow-white (approximately 158C-D) to orange-white (159C-D). Pollen abundant, color approximately 158A-C.

Roots: main roots thick, fleshy. Abundant fine lateral roots, white to cream.

Flowering: Flowers naturally in 15 cm pots, approximately 7–9 months from planting tissue culture produced microcuttings, producing good quality inflorescences from the onset of flowering. At approximately 16 months two to six white spathes present above foliage.

Disease and insect resistance: No unusual susceptibility to diseases or insects noted to date.

Comparison with known cultivars:

The new cultivar can be compared to the known cultivars 'Viscount' (unpatented) and 'Petite'(unpatented).

'S2' is distinguished from the both cultivars by its earlier flowering (8 months after planting tissue culture produced microcuttings 90% of 'S2' plants flowered but not any of 'Petite' or 'Viscount'); more abundant, year round natural flowering (16 months after planting microcuttings plants of 'S2' had 2–6 spathes, 'Viscount' had 0–2 and 'Petite' none); better quality of first inflorescences; stronger and more upright peduncles; larger spathes.

'S2' is further distinguished from 'Viscount' by its slightly smaller size and smaller, slightly lighter green leaf blades.

'S2' is further distinguished from 'Petite' by its larger size; more open growth habit; lesser branching; larger leaf blades; thicker peduncles. The new cultivar can also be compared to the sibling cultivar 'S16', which is described in co-pending U.S. Plant Patent Application Ser. No. 08/859, 466. 'S2' is distinguished from 'S16' by its less abundant branching; its more open and more upright growth habit; slightly darker green leaves, that are more elliptic, narrower in proportion to their length and have more cuneate bases; by the spathes that are situated slightly higher above foliage, are slightly more elliptic and have slightly more cuneate bases.

I claim:

1. A new and distinct cultivar of Spathiphyllum plant named 'S2', substantially as described and illustrated herein, characterized particularly as to novelty by its medium to large size; relatively open and upright growth habit; vigorous growth; early branching; early, abundant and year-round natural flowering; inflorescences of a superior quality from the onset of flowering; large spathes held on thick, strong peduncles.

* * * * *